United States Patent
Colborn et al.

(10) Patent No.: US 8,849,409 B2
(45) Date of Patent: *Sep. 30, 2014

(54) DYNAMIC CRANIAL NERVE STIMULATION BASED ON BRAIN STATE DETERMINATION FROM CARDIAC DATA

(71) Applicants: Cyberonics, Inc., Houston, TX (US); Flint Hills Scientific, LLC, Lawrence, KS (US)

(72) Inventors: John C. Colborn, League City, TX (US); Mark G. Frei, Oviedo, FL (US); Ivan Osorio, Leawood, KS (US)

(73) Assignees: Cyberonics, Inc., Houston, TX (US); Flint Hills Scientific, LLC, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/783,393

(22) Filed: Mar. 3, 2013

(65) Prior Publication Data
US 2013/0204144 A1    Aug. 8, 2013

Related U.S. Application Data

(63) Continuation of application No. 12/258,019, filed on Oct. 24, 2008, now Pat. No. 8,417,344.

(51) Int. Cl.
*A61N 1/00* (2006.01)
*A61B 5/0205* (2006.01)
*A61B 5/04* (2006.01)
*A61N 1/36* (2006.01)

(52) U.S. Cl.
CPC .......... *A61B 5/0205* (2013.01); *A61N 1/36114* (2013.01); *A61N 1/36082* (2013.01); *A61B 5/04012* (2013.01)
USPC .......................................................... 607/45

(58) Field of Classification Search
USPC ........................................................... 607/45
See application file for complete search history.

(56) References Cited

U.S. PATENT DOCUMENTS

| 4,172,459 A | 10/1979 | Hepp |
| 4,291,699 A | 9/1981 | Geddes et al. |

(Continued)

FOREIGN PATENT DOCUMENTS

| EP | 1145736 | 10/2001 |
| EP | 1486232 | 12/2004 |

(Continued)

OTHER PUBLICATIONS

Bachman, D.,S. et al.; "*Effects of Vagal Volleys and Serotonin on Units of Cingulate Cortex in Monkeys*;" Brain Research, vol. 130 (1977). pp. 253-269.

(Continued)

*Primary Examiner* — George Manuel

(57) ABSTRACT

A method of treating a medical condition in a patient using an implantable medical device, comprising providing an electrical signal generator; providing at least a first electrode operatively coupled to the electrical signal generator and to a vagus nerve of the patient; sensing cardiac data of the patient; determining at least a first cardiac parameter based upon said cardiac data; setting at least a first value; declaring an unstable brain state of a patient from said at least a first cardiac parameter and said at least a first value; and adjusting the at least a first value. Also, a computer readable program storage device encoded with instructions that, when executed by a computer, performs the method. In addition, the implantable medical device used in the method.

20 Claims, 6 Drawing Sheets

(56) References Cited

U.S. PATENT DOCUMENTS

| | | |
|---|---|---|
| 4,541,432 A | 9/1985 | Molina-Negro et al. |
| 4,573,481 A | 3/1986 | Bullara |
| 4,702,254 A | 10/1987 | Zabara |
| 4,867,164 A | 9/1989 | Zabara |
| 4,920,979 A | 5/1990 | Bullara |
| 4,949,721 A | 8/1990 | Toriu et al. |
| 4,979,511 A | 12/1990 | Terry, Jr. |
| 5,025,807 A | 6/1991 | Zabara |
| 5,113,869 A | 5/1992 | Nappholz et al. |
| 5,137,020 A | 8/1992 | Wayne et al. |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,522,862 A | 6/1996 | Testerman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise et al. |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,792,186 A | 8/1998 | Rise |
| 5,800,474 A | 9/1998 | Benabid et al. |
| 5,833,709 A | 11/1998 | Rise et al. |
| 5,913,876 A | 6/1999 | Taylor et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,987,352 A | 11/1999 | Klein et al. |
| 5,995,868 A | 11/1999 | Osorio et al. |
| 6,016,449 A | 1/2000 | Fischell et al. |
| 6,018,682 A | 1/2000 | Rise |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,768,969 B1 | 7/2004 | Nikitin et al. |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,885,888 B2 | 4/2005 | Rezai |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,934,585 B1 | 8/2005 | Schloss |
| 6,944,501 B1 | 9/2005 | Pless |

(56) References Cited

U.S. PATENT DOCUMENTS

| | | |
|---|---|---|
| 6,957,107 B2 | 10/2005 | Rogers |
| 6,961,618 B2 | 11/2005 | Osorio et al. |
| 6,985,771 B2 | 1/2006 | Fischell et al. |
| 6,990,377 B2 | 1/2006 | Gliner et al. |
| 7,006,859 B1 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,054,792 B2 | 5/2006 | Frei et al. |
| 7,058,453 B2 | 6/2006 | Nelson et al. |
| 7,076,288 B2 | 7/2006 | Skinner |
| 7,079,977 B2 | 7/2006 | Osorio et al. |
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,321,837 B2 | 1/2008 | Osorio et al. |
| 7,324,850 B2 | 1/2008 | Persen et al. |
| 7,324,851 B1 | 1/2008 | DiLorenzo |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,366,571 B2 * | 4/2008 | Armstrong .............. 607/45 |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,433,732 B1 | 10/2008 | Carney et al. |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0088024 A1 | 5/2004 | Firlik et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |

(56) References Cited

U.S. PATENT DOCUMENTS

| | | |
|---|---|---|
| 2006/0200206 A1 | 9/2006 | Firlik et al. |
| 2006/0212091 A1 | 9/2006 | Lozano et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong et al. |
| 2007/0027497 A1 | 2/2007 | Parnis |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |

FOREIGN PATENT DOCUMENTS

| | | |
|---|---|---|
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

Baevskii, R.M. "*Analysis of Heart Rate Variability in Space Medicine*;" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station*;" J. Applied Physiological, vol. 103, (2007) pp. 156-161.

Boon, P., et al.; "*Vagus Nerve Stimulation for Epilepsy, Clinical Efficacy of Programmed and Magnet Stimulation*;" (2001); pp. 93-98.

Boon, Paul, et al.; "*Programmed and Magnet-Induced Vagus Nerve Stimulation for Refractory Epilepsy*;" Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin*;" Letters to Nature; vol. 405; (May 2000); pp. 458-462.

Brack, Kieran E., et al.; "*Interaction Between Direct Sympathetic and Vagus Nerve Stimulation on Heart Rate in the Isolated Rabbit Heart*;" Experimental Physiology vol. 89, No. 1; pp. 128-139.

Chakravarthy, N., et al.; "*Controlling Synchronization in a Neuron-Level Population Model*;" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat*;" Neurobiology of Learning and Memory, vol. 70, 364-373 (1998) Art. No. NL983863.

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and on Its Variability in Humans:*" Epilepsia, vol. 42, No. 8 (2001); pp. 1007-1016.

George, M.S., et al.; "*Vagus Nerve Stimulation: A New Tool for Brain Research and Therapy*;" Society of Biological Psychiatry vol. 47 (2000) pp. 287-295.

"*Heart Rate Variability—Standards of Measurement, Physiological Interpretation, and Clinical Use*" Circulation—Electrophysiology vol. 93, No. 5; http://circ.ahajournals.org/cgi/content-nw/full/93/5/1043/F3.

Henry, Thomas R.; "*Therapeutic Mechanisms of Vague Name Stimulation*;". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys*;" Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques*;" IEEE Transactions on Biomedical Engineering, vol. 51, No. 3 (Mar. 2004); pp. 493-506.

Iasemidis; L.D., et al.; "*Spatiotemporal Transition to Epileptic Seizures: A Nonlinear Dynamical Analysis of Scalp and Intracranial EEG Recordings*;" Spatiotemporal Models in Biological and Artificial Systems; F.L. Silva et al. (Eds.) IOS Press, 1997; pp. 81-88.

Iasemidis, L.D.; "*Epileptic Seizure Prediction and Control*" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*" Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press—YSEIZ-1305; pp. 1-4.

(56) References Cited

OTHER PUBLICATIONS

Koo, B., "*EEG Changes With Vagus Nerve Stimulation*" Journal of Clinical Neurophysiology, vol. 18 No. 5 (Sep. 2001); pp. 434-441.

Krittayaphong, M.D., et al.; "*Heart Rate Variability in Patients with Coronary Artery Disease: Differences in Patients with Higher and Lower Depression Scores*" Psychosomatic Medicine vol. 59 (1997) pp. 231-235.

Leutmezer, F., et al.; "*Electrocardiographic Changes at the Onset of Epileptic Seizures*;" Epilepsia, vol. 44, No. 3; (2003); pp. 348-354.

Lewis, M.E., et al.; "*Vagus Nerve Stimulation Decreases Left Ventricular Contractility in Vivo in the Human and Pig Heart*" The Journal of Physiology vol. 534, No. 2, (2001) pp. 547-552.

Li, M., et al.; "*Vagal Nerve Stimulation Markedly Improves Long-Term Survival After Chronic Heart Failure in Rats*;" Circulation (Jan. 2004) pp. 120-124.

Licht, C.M.M.; *Association Between Major Depressive Disorder and Heart Rate Variability in the Netherlands Study of Depression and Anxiety (NESDA)*; Arch. Gen Psychiatry, vol. 65, No. 12 (Dec. 2008); pp. 1358-1367.

Lockard et al., "*Feasibility and Safety of Vagal Stimulation in Monkey Model*;" Epilepsia, vol. 31 (Supp. 2) (1990), pp. S20-S26.

McClintock, P., "*Can Noise Actually Boost Brain Power*" Physics World Jul. 2002; pp. 20-21.

Mori, T., et al.; "*Noise-Induced Entrainment and Stochastic Resonance in Human Brain Waves*" Physical Review Letters vol. 88, No. 21 (2002); pp. 218101-1-218101-4.

Mormann, F., "Seizure prediction: the long and winding road," Brain 130 (2007), 314-333.

Nouri, M.D.; "*Epilepsy and the Autonomic Nervous System*" emedicine (updated May 5, 2006); pp. 1-14; http://www.emedicine.com/neuro/topic658.htm.

O'Regan, M.E., et al.; "*Abnormalities in Cardiac and Respiratory Function Observed During Seizures in Childhood*" Developmental Medicine & Child Neurlogy, vol. 47 (2005) pp. 4-9.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "*Complex Estimation of Adaptation Abilities of the Organism in Children Using the Indices of Responsiveness of the Cardiovascular System and Characteristics of EEG*" Neurophysiology vol. 38, No. 1 (2006); pp. 63-74.

Rugg-Gunn, F.J., et al.; "*Cardiac Arrhythmias in Focal Epilepsy: a Prospective Long-Term Study*" www.thelancet.com vol. 364 (2004) pp. 2212-2219.

Sajadieh, A., et al.; "*Increased Heart Rate and Reduced Heart-Rte Variability are Associated with Subclinical Inflammation in Middle-Aged and Elderly Subjects with No Apparent Heart Disease*" European Heart Journal vol. 25, (2004); pp. 363-370.

Schernthaner, C., et al.; "*Autonomic Epilepsy—The Influence of Epileptic Discharges on Heart Rate and Rhythm*" The Middle European Joural of Medicine vol. 111, No. 10 (1999) pp. 392-401.

Terry et al.; "*The Implantable Neurocybernetic Prosthesis System*", Pacing and Clinical Electrophysiology, vol. 14, No. 1 (Jan. 1991), pp. 86-93.

Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.

Umetani, M.D., et al.; "*Twenty-Four Hour Time Domain Heart Rate Variability and Heart Rate: Relations to Age and Gender Over Nince Decades*" JACC vol. 31, No. 3; (Mar. 1998); pp. 593-601.

Vonck, K., et al. "*The Mechanism of Action of Vagus Nerve Stimulation for Refractory Epilepsy—The Current Status*", Journal of Neurophysiology, vol. 18 No. 5 (2001), pp. 394-401.

Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.

Zabara, J.; "*Neuroinhibition of Xylaine Induced Emesis*" Pharmacology & Toxicology, vol. 63 (1988) pp. 70-74.

Zabara, J. "*Inhibition of Experimental Seizures in Canines by Repetivie Vagal Stimulation*" Epilepsia vol. 33, No. 6 (1992); pp. 1005-1012.

Zabara, J., et al.; "*Neural Control of Circulation I*" The Physiologist, vol. 28 No. 4 (1985); 1 page.

Zabara, J., et al.; "*Neuroinhibition in the Regulation of Emesis*" Space Life Sciences, vol. 3 (1972) pp. 282-292.

Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.

Osorio, Ivan et al., "Automated Seizure Abaatement in Humans Using Electrical Stimulation," Annals of Neurology, vol. 57, No. 2, pp. 258-268, 2005.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Weil, Sabine et al, "Heart Rate Increase in Otherwise Sublinical Seizures Is Different in Temporal Versus Extratemporal Seizure Onset: Support for Temporal Lobe Automatic Influence," Epileptic Disord., vol. 7, No. 3, Sep. 2005, pp. 199-204.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

O'Donovan, Cormac A. et al., "Computerized Seizure Detection Based on Heart Rate Changes," abstract of AES Proceedings, Epilepsia, vol. 36, Suppl. 4, 1995, p. 7.

Robinson, Stephen E et al., "Heart Rate Variability Changes as Predictor of Response to Vagal Nerve Stimulation Therapy for Epilepsy," abstract of AES Proceedings, Epilepsia, vol. 40, Suppl. 7, 1999, p. 147.

Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

\* cited by examiner

DYNAMIC CRANIAL NERVE STIMULATION BASED ON BRAIN STATE DETERMINATION FROM CARDIAC DATA

This application is a continuation application of U.S. patent application Ser. No. 12/258,019, filed Apr. 29, 2010 and is hereby incorporated herein by reference in its entirety.

BACKGROUND OF THE INVENTION

This invention relates generally to medical device systems and, more particularly, to medical device systems for applying electrical signals to a cranial nerve for the treatment of various medical conditions exhibiting unstable brain states as determined by analysis of data from a patient's cardiac cycle.

Many advancements have been made in treating medical conditions involving or mediated by the neurological systems and structures of the human body. In addition to drugs and surgical intervention, therapies using electrical signals for modulating electrical activity of the body have been found to be effective for many medical conditions. In particular, medical devices have been effectively used to deliver therapeutic electrical signals to various portions of a patient's body (e.g., the vagus nerve) for treating a variety of medical conditions. Electrical signal therapy may be applied to a target portion of the body by an implantable medical device (IMD) that is located inside the patient's body or, alternatively, may be applied by devices located external to the body. In addition, some proposed devices include a combination of implanted and external components.

The vagus nerve (cranial nerve X) is the longest nerve in the human body. It originates in the brainstem and extends, through the jugular foramen, down below the head, to the abdomen. Branches of the vagus nerve innervate various organs of the body, including the heart, the stomach, the lungs, the kidneys, the pancreas, and the liver. In view of the vagus nerve's many functions, a medical device such as an electrical signal generator has been coupled to a patient's vagus nerve to treat a number of medical conditions. In particular, electrical signal therapy for the vagus nerve, often referred to as vagus nerve stimulation (VNS), has been approved in the United States and elsewhere to treat epilepsy and depression. In particular, application of an electrical signal to the vagus nerve is thought to modulate some areas in the brain that are prone to seizure activity.

Implantable medical devices (IMDs) have been effectively used to deliver therapeutic stimulation to various portions of the human body (e.g., the vagus nerve) for treating a variety of diseases. As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

In some embodiments, electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. In yet another type of stimulation, both passive stimulation and feedback stimulation may be combined, in which electrical signals are delivered passively according to a predetermined duty cycle, and also in response to a sensed body parameter indicating a need for therapy. The electrical signal may be applied by a pulse generator that is implanted within the patient's body. In another alternative embodiment, the signal may be generated by an external pulse generator outside the patient's body, coupled by an RF or wireless link to an implanted electrode or an external transcutaneous neurostimulator (TNS).

Generally, neurostimulation signals that perform neuromodulation are delivered by the IMD via one (i.e., unipolar) or more (i.e., bipolar) leads. The leads generally terminate at their distal ends in one or more electrodes, and the electrodes, in turn, are electrically coupled to tissue in the patient's body. For example, a number of electrodes may be attached to various points of a nerve or other tissue inside or outside a human body for delivery of a neurostimulation signal.

Conventional vagus nerve stimulation (VNS) usually involves non-feedback stimulation characterized by a number of parameters. Specifically, conventional vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 7-60 seconds. The pulse bursts are separated from one another by the off-time, (e.g., 14 seconds-5 minutes) in which no electrical signal is applied to the nerve. The on-time and off-time parameters together define a duty cycle, which is the ratio of the on-time to the sum of the on-time and off-time, and which describes the percentage of time that the electrical signal is applied to the nerve. It will be appreciated that calculation of duty cycle should also include any ramp-up and/or ramp-down time.

In conventional VNS, the on-time and off-time may be programmed to define an intermittent pattern in which a repeating series of electrical pulse bursts are generated and applied to the vagus nerve 127. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

Although neurostimulation has proven effective in the treatment of a number of medical conditions, including epilepsy, it would be desirable to further enhance and optimize a therapeutic regimen comprising neurostimulation for this purpose. For example, it may be desirable to provide an active therapeutic regimen at times when an unstable brain state occurs. (An "unstable brain state" will be defined below). It may also be desirable to declare an unstable brain state as occurring, based on data routinely collected from extracranial sources. It may further be desirable to adjust the sensitivity of declaring when an unstable brain state occurs, to make a declaration of an unstable brain state more or less likely for different patients, for the same patient at different times of day, month, or year, or under other conditions.

SUMMARY OF THE INVENTION

In one embodiment, the present invention relates to an implantable medical device (IMD) to treat a medical condition in a patient, comprising an electrical signal generator; at least a first electrode operatively coupled to the electrical signal generator and to a vagus nerve of the patient; a cardiac data sensing module capable of sensing cardiac data from the patient; an unstable brain state declaration module comprising a cardiac module capable of determining at least a first cardiac parameter based upon sensed cardiac data from the patient; and a value setting module for setting at least a first value to be used by the unstable brain state declaration module; wherein the unstable brain state declaration module is capable of declaring an unstable brain state of a patient from said at least a first cardiac parameter and said at least a first value and the value setting module is capable of adjusting said at least a first value.

In one embodiment, the present invention relates to a method of treating a medical condition in a patient using an implantable medical device, comprising providing an electrical signal generator; providing at least a first electrode operatively coupled to the electrical signal generator and to a vagus nerve of the patient; sensing cardiac data of the patient; determining at least a first cardiac parameter based upon said cardiac data; setting at least a first value; declaring an unstable brain state of a patient from said at least a first cardiac parameter and said at least a first value; and adjusting said at least a first value.

In one embodiment, the present invention relates to a computer readable program storage device encoded with instructions that, when executed by a computer, performs a method of treating a medical condition in a patient using an implantable medical device, comprising providing an electrical signal generator; providing at least a first electrode operatively coupled to the electrical signal generator and to a vagus nerve of the patient; sensing cardiac data of the patient; determining at least a first cardiac parameter based upon said cardiac data; setting at least a first value; declaring an unstable brain state of a patient from said at least a first cardiac parameter and said at least a first value; and adjusting said at least a first value.

BRIEF DESCRIPTION OF THE DRAWINGS

The invention may be understood by reference to the following description taken in conjunction with the accompanying drawings, in which like reference numerals identify like elements, and in which.

Figure 1A:
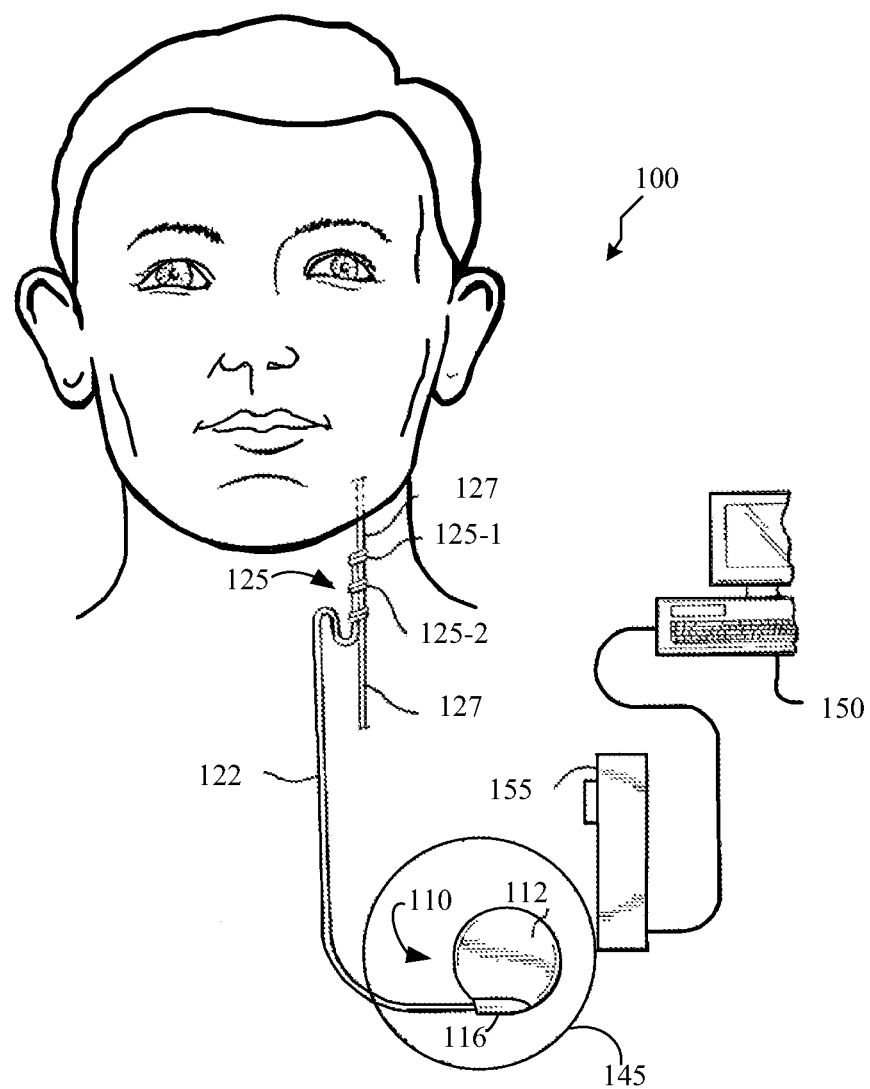
FIGS. 1A-1C provide stylized diagrams of an implantable medical device implanted into a patient's body for providing an electrical signal to a portion of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

"Cardiac cycle" refers to one complete PQRSTU interval of the patient's heart functioning, ending with the P wave of the next succeeding cardiac cycle. "Interbeat interval" refers to the time period between a predetermined point in a first cardiac cycle of the patient and the same predetermined point in the immediately succeeding cardiac cycle of the patient, for example an R-R interval, a P-P interval, or a T-T interval. Interbeat intervals may comprise a single interval or a time-varying statistic, such as a moving average (either simple or weighted) of several consecutive intervals. "Cardiac period" is a length of time between a first point in the cardiac cycle of the patient and a second, later point. Exemplary points include a P-wave, a Q-wave, an R-wave, an S-wave, a T-wave, and a U-wave of the cardiac cycle, which can be readily identified by electrocardiography (EKG) or other techniques of monitoring the electrical activity of the heart.

Any method step referring to the storing, recalling, manipulating, or changing of data, a parameter, or a value is to be understood as referring to making physical changes in an apparatus, such as an implantable medical device or an external apparatus in communication with an implantable medical device; such method steps do not refer to any purely mental step performed in the mind of a human being.

Cranial nerve stimulation has been proposed to treat a number of medical conditions pertaining to or mediated by one or more neural structures of the body, including epilepsy and other movement disorders, depression, anxiety disorders and other neuropsychiatric disorders, dementia, head trauma and traumatic brain injury, coma, obesity, eating disorders, sleep disorders, cardiac disorders (such as congestive heart failure and atrial fibrillation), hypertension, endocrine disorders (such as diabetes and hypoglycemia), and pain syndromes (including migraine headache and fibromyalgia), among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, the precise stimulation parameters that would modulate particular pathways relevant to a particular disorder generally cannot be predicted.

In one embodiment, the present invention provides a method of treating a medical condition. The medical condition can be selected from the group consisting of epilepsy, neuropsychiatric disorders (including but not limited to depression), eating disorders/obesity, traumatic brain injury/coma, addiction disorders, dementia, sleep disorders, pain, migraine, fibromyalgia, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including infertility). In a particular embodiment, the medical condition is epilepsy.

The implantable medical device (IMD) system of one embodiment of the present invention provides for module(s) that are capable of acquiring, storing, and processing one or more of various forms of data, such as patient cardiac data or a cardiac parameter (e.g., heart rate, rate of change of heart rate, etc.), at least one value used to declare an unstable brain state of a patient, declarations of unstable brain states, logs of timestamped cardiac data, cardiac parameters, and therapy parameters. Therapy parameters may include, but are not limited to, electrical signal parameters that define the therapeutic electrical signals delivered by the IMD, medication parameters, and/or any other therapeutic treatment parameter. Therapy parameters defining a therapeutic electrical signal may also include, but are not limited to, a current amplitude, a pulse width, an interburst period, a number of pulses per burst, an interpulse interval, a burst duration, an on-time, and an off-time. "Therapy parameters" encompasses one or multiple treatment regimens (e.g., different electrical signals), wherein the multiple treatment regimens may differ in one or more therapy parameters.

Figure 1B:
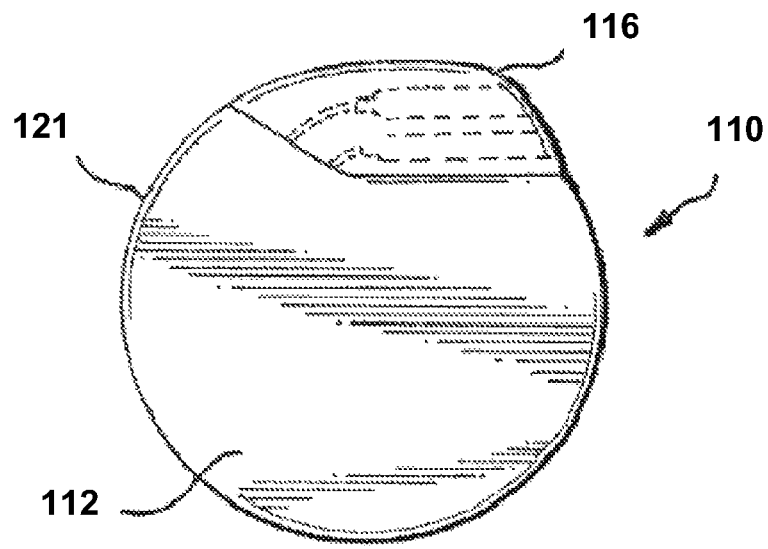
Figure 1C:
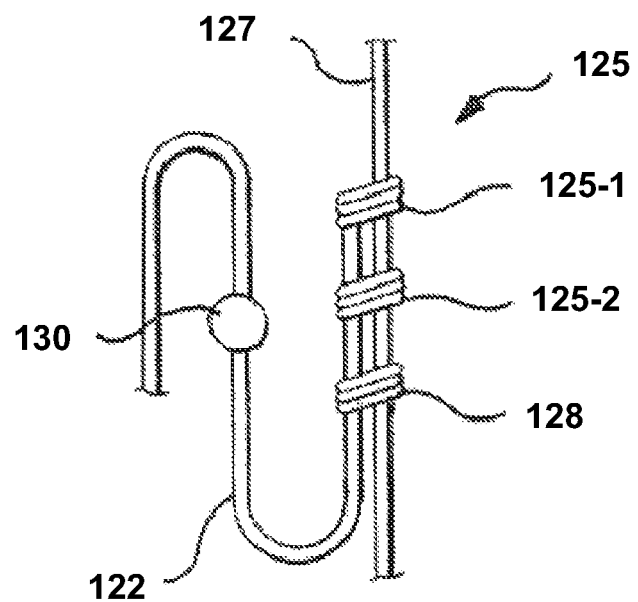

Although not so limited, a system capable of implementing embodiments of the present invention is described below. FIG. 1 depicts a stylized implantable medical system (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity 145 formed by the implanting surgeon just below the skin, similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes with the return electrode comprising a portion of the generator 110.

Lead assembly 122 is attached at its proximal end to connectors on the header 116 of generator 110. The electrode assembly 125 may be surgically coupled to the vagus nerve 127 in the patient's neck or at another location, e.g., near the patient's diaphragm or at the esophagus/stomach junction. Other (or additional) cranial nerves such as the trigeminal and/or glossopharyngeal nerves may also be used as a target for the electrical signal in particular alternative embodiments. In one embodiment, the electrode assembly 125 comprises a bipolar stimulating electrode pair 125-1, 125-2 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the vagus nerve 127 by a spiral anchoring tether 128 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection 130 to nearby tissue (not shown).

In alternative embodiments, the electrode assembly 125 may comprise a cardiac data sensor element. Alternatively, a cardiac data sensor element may be contained in a separate sensing electrode assembly (not shown). One or more other sensor elements for other body parameters may also be included in the electrode assembly 125 or in a separate sensing electrode assembly (not shown). For example, motion sensors or electrodes may be used to sense respiration, and pressure sensors or neural activity may be used to sense blood pressure. Both passive and active stimulation may be combined or delivered by a single IMD according to the present invention. Either or both modes may be appropriate to treat a specific patient under observation.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The therapeutic electrical stimulation signal described herein may be used to treat a medical condition separately or in combination with another type of treatment. For example, electrical signals according to the present invention may be applied in combination with a chemical agent, such as various drugs, to treat various medical conditions. Further, the electrical stimulation may be performed in combination with treatment(s) relating to a biological or chemical agent. The electrical stimulation treatment may also be performed in combination with other types of treatment, such as magnetic stimulation treatment.

Figure 2:
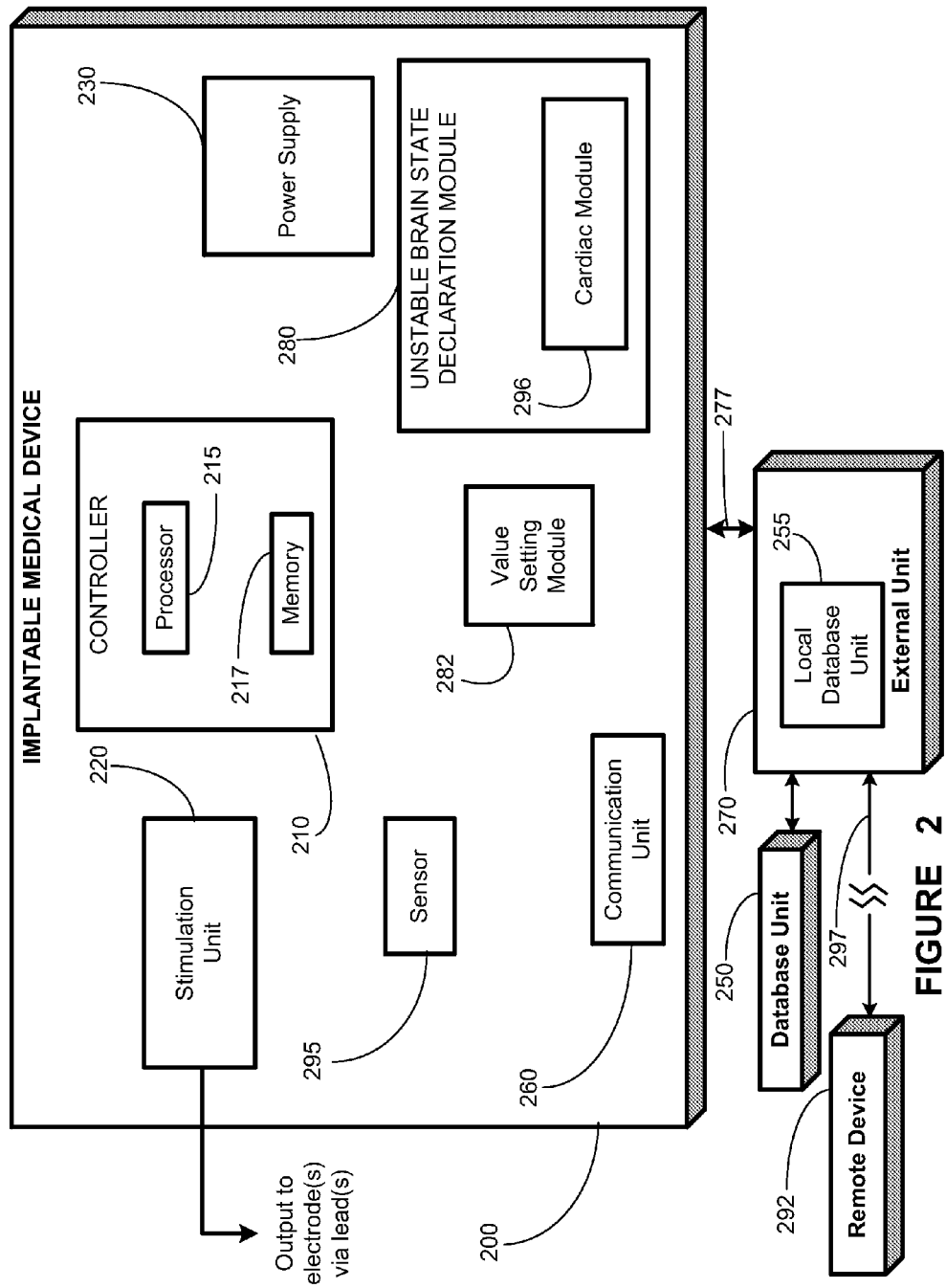
FIG. 2 illustrates a block diagram depiction of the implantable medical device of FIG. 1, in accordance with one illustrative embodiment of the present invention.

Turning now to FIG. 2, a block diagram depiction of the IMD 200 is provided, in accordance with one illustrative embodiment of the present invention. The IMD 200 (which may be equivalent to generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering an electrical signal over the leads comprising the lead assembly 122. It will be appreciated by persons of skill in the art that some embodiments of the invention may comprise leadless stimulators such as injectable microstimulators.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 that may comprise an ED (FIG. 1). The communication unit 260 may include hardware, software, firmware, or any combination thereof.

In one embodiment, the IMD 200 may also comprise a sensor 295 that is capable of detecting various patient parameters. For example, the sensor 295 may comprise hardware, software, firmware, or any combination thereof that is capable of obtaining and/or analyzing data relating to one or more physiological parameters of the patient, such as at least one cardiac parameter. In one embodiment, the lead assembly 122 and electrode(s) 125 may function as the sensor 295. In another embodiment, the sensor 295 is a separate structure from the lead assembly 122 and electrode(s) 125. In one embodiment, the sensor 295 may reside external to the IMD 200 and the sensed results may be delivered to the IMD 200 via wire, telemetry, or other techniques known in the art. Based upon the data obtained by the sensor 295, an cardiac module 296 may determine the at least one cardiac parameter.

In one embodiment, the sensor 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient.

In one embodiment, the sensor 295 may be capable of sensing cardiac data and the cardiac module 296 may be capable of determining at least one cardiac parameter of the patient from the sensed cardiac data. However, in another embodiment, a separate sensor 295 is not included, and sensing cardiac data of the patient may be performed via one or more of the electrodes 125(1), 125(2) and/or the shell 112 of the IMD 200.

Figure 3:
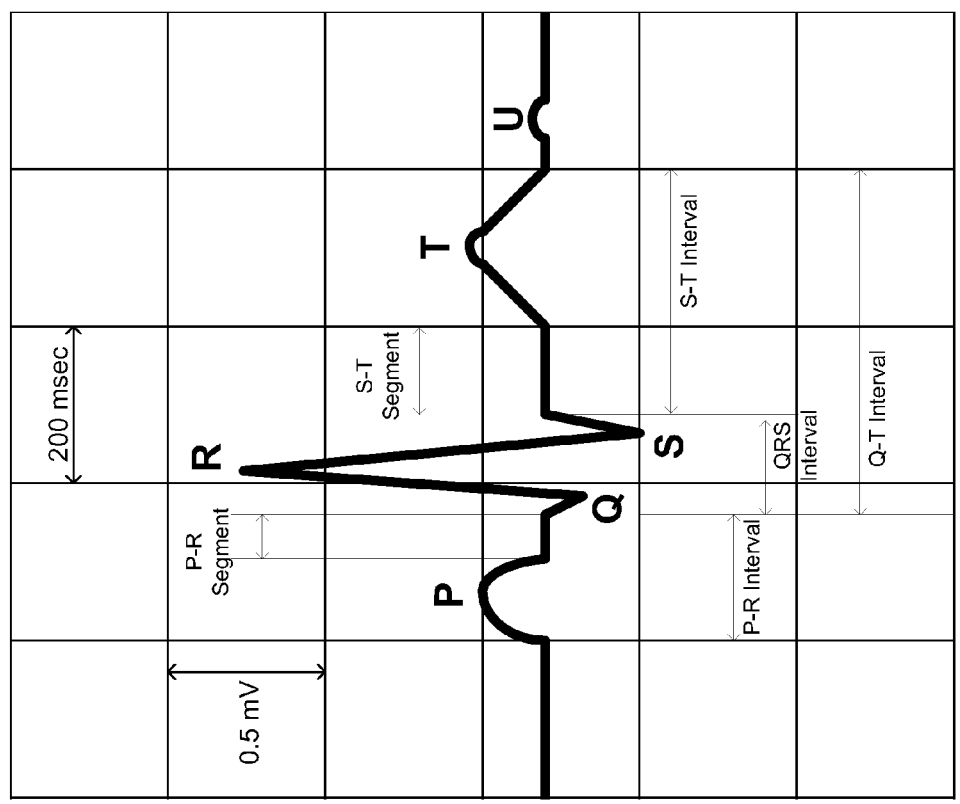
FIG. 3 illustrates an exemplary waveform sequence of a cardiac cycle of a human being as measured by an electrocardiogram (EKG)

Cardiac data may be sensed at any point in the patient's cardiac cycle. FIG. 3 shows an exemplary instance of the cardiac cycle in a human being.

The cardiac module 296 may be capable of determining a first cardiac parameter consisting of an interbeat interval. The cardiac module 296 may further be capable of determining a first cardiac parameter consisting of an instantaneous heart rate, that is, the reciprocal of a single interbeat interval, which may be normalized to a unit time, such as one minute. For example, if the interbeat interval is determined as an R-R interval, and a single R-R interval is 800 msec, the reciprocal is 0.00125 msec-1, or 1.25 sec-1, or 75 min-1 (75 BPM).

The cardiac module 296 may be capable of determining a first cardiac parameter consisting of a moving average heart rate over a predetermined time period. The moving average heart rate may be a simple moving average, that is, the average of the reciprocal of n consecutive interbeat intervals, wherein n is an integer from 2 to about 20, such as 3 to 10.

The cardiac module 296 may be capable of determining a first cardiac parameter consisting of a rate of change of the patient's heart rate, which may be determined from a series of values of either an instantaneous heart rate or a moving average heart rate.

The cardiac module 296 may be capable of determining an elevation of a patient's heart rate above the patient's baseline heart rate. For example, a baseline heart rate may be defined as a 30-beat moving average heart rate, or longer moving average such as a 5 minute average heart rate, and the elevation may be the difference between an instantaneous heart rate and the baseline rate. Cardiac module 296 may further be capable of determining a difference between a first moving average and a second moving average. The first and second moving averages may be based upon a particular number of beats, for example a 3 beat moving average and a 30 beat moving average, or upon particular time periods, for example a 10 second moving average and a 5 minute moving average. In another embodiment, cardiac module 296 may be capable of determining a first cardiac parameter consisting of a duration of an elevation of the patient's heart rate above the patient's baseline heart rate. The patient's baseline heart rate may be determined by a medical professional at an initial calibration or subsequent recalibration of the IMD 200 or may be determined by the IMD 200 itself, such as a long term moving average of the heart rate. The long term moving average can be calculated with the exclusion of cardiac data from times recognized, either at the time or retrospectively, as being associated with an unstable brain state. "Unstable brain state" will be discussed below.

The cardiac module 296 may be capable of determining a first cardiac parameter consisting of a depression of the patient's heart rate below the patient's baseline heart rate.

The cardiac module 296 may be capable of determining a first cardiac parameter consisting of a duration of an elevation of a first moving average heart rate over a second moving average heart rate.

The cardiac module 296 may be capable of determining a first cardiac parameter consisting of an R-R interval.

The cardiac module 296 may be capable of determining a first cardiac parameter consisting of a PR segment interval.

The cardiac module 296 may be capable of determining a first cardiac parameter consisting of a PQ segment interval.

The cardiac module 296 may be capable of determining a first cardiac parameter consisting of a QRS interval.

The cardiac module 296 may be capable of determining a first cardiac parameter consisting of an ST segment interval.

The cardiac module 296 may be capable of determining a first cardiac parameter consisting of a statistical analysis heart parameter, such as a median, a standard deviation, or another statistical analysis value known to the person of ordinary skill in the art to be extractable or calculable from a stream of cardiac data.

The cardiac module 296 may be capable of determining a first cardiac parameter consisting of the amplitude or magnitude of the P wave, Q wave, R wave, S wave, T wave, U wave, or any segment or interval between waves; a change of the amplitude or magnitude of the wave or any segment or interval between waves; or a rate of change of the amplitude or magnitude of the wave or any segment or interval between waves. The amplitude or magnitude of a segment or interval encompasses the absolute difference in amplitude or magnitude of the waves defining the endpoints of the segment or interval and the relative difference in amplitude or magnitude of the waves defining the endpoints of the segment or interval, among other parameters.

The cardiac module 296 may be capable of determining a first cardiac parameter consisting of a spectral analysis heart parameter.

The cardiac module 296 may be capable of determining a first cardiac parameter consisting of a fractal analysis heart parameter.

In one embodiment, at least a first cardiac parameter is selected from the group consisting of an instantaneous heart rate, a moving average heart rate over a predetermined time period, a ratio of a first moving average heart rate over a first predetermined time period and a second moving average heart rate over a second predetermined time period, a rate of change of the patient's heart rate, an elevation of the patient's instantaneous heart rate above a baseline heart rate, a duration of an elevation of the patient's heart rate above the patient's baseline heart rate, a depression of the patient's heart rate below the patient's baseline heart rate, a duration of an elevation of a first moving average heart rate over a second moving average heart rate, an R-R interval, a PR segment interval, a PQ segment interval, a QRS interval, an ST segment interval, a QT interval, a statistical analysis heart parameter, a spectral analysis heart parameter, a fractal analysis heart parameter, an interbeat interval, the amplitude or magnitude of the P wave, Q wave, R wave, S wave, T wave, U wave, or any segment or interval between waves; a change of the amplitude or magnitude of the wave or any segment or interval between waves; or a rate of change of the amplitude or magnitude of the wave or any segment or interval between waves, and two or more thereof.

The external unit 270 may be a device that is capable of programming the IMD 200 with parameters defining the electrical signal. In one embodiment, the external unit 270 is a computer system capable of executing a data-acquisition program. The external unit 270 may be controlled by a healthcare provider, such as a physician, at a base station in, for example, a doctor's office, or via telemetry from a doctor's office to a patient's home. In alternative embodiments, the external unit 270 may be controlled by a patient in a system. In patient-controlled systems, the external unit 270 may provide less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may upload various parameters and program software into the IMD 200 for programming the operation of the IMD, and may also receive and download various status conditions and other data from the IMD 200. Communications between the external unit 270 and the communication unit 260 in the IMD 200 may occur via a wireless or other type of communication, represented generally by line 277 in FIG. 2. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various data. This data may comprise cardiac data acquired from a patient's body, at least one cardiac parameter derived from the cardiac data, other data acquired from a patient's body, at least one non-cardiac parameter derived from the other data, at least a first value as will be discussed below, and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions using the external unit 270, which may include obtaining and/or analyzing data from the IMD 200 and/or data from the database unit 250 and/or the local database unit 255. The database unit 250 and/or the local database unit 255 may store various patient data.

One or more of the blocks illustrated in the block diagram of the IMD 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110. Two taps spaced apart by a slightly longer duration of time may be programmed into the IMD 100 to indicate a desire to deactivate the electrical signal generator 110, for example. The patient may be given limited control over operation of the device to an extent determined by the program dictated or entered by the attending physician. The patient may also activate the IMD 100 using other suitable techniques or apparatus.

In one embodiment, the present invention relates to an implantable medical device (IMD) to treat a medical condition in a patient, comprising an electrical signal generator 220; at least a first electrode 125-1 operatively coupled to the electrical signal generator and to a vagus nerve 127 of the patient; a cardiac data sensing module 295 capable of sensing cardiac data from the patient; an unstable brain state declaration module 280 comprising a cardiac module 296 capable of determining at least a first cardiac parameter based upon sensed cardiac data from the patient; and a value setting module 282 for setting at least a first value to be used by the unstable brain state declaration module 280; wherein the unstable brain state declaration module 280 is capable of declaring an unstable brain state of a patient from said at least a first cardiac parameter and said at least a first value and the value setting module 282 is capable of adjusting said at least a first value.

The electrical signal generator 220 has been described above, as has the at least a first electrode 125-1 operatively coupled to the electrical signal generator 220 and to a vagus nerve 127 of the patient and the cardiac data sensing module 295 capable of sensing cardiac data from the patient.

The IMD 200 comprises an unstable brain state declaration module 280 that, in turn, comprises a cardiac module 296 capable of determining at least a first cardiac parameter based upon sensed cardiac data from the patient. IMD 200 further comprises a value setting module 282 for setting at least a first value to be used by the unstable brain state declaration module 280. The unstable brain state declaration module 280 is capable of declaring an unstable brain state of a patient from said at least a first cardiac parameter and said at least a first value.

An "unstable brain state" is used herein to refer to the state of the brain during an epileptic seizure, the state of the brain during an aura, the state of the brain during a post-ictal period after an epileptic seizure, or any other state of the brain associated with the increased likelihood of a seizure in the near future (within from about 1 sec to about 12 hr, such as from about 5 sec to about 1 hr, such as from about 10 sec to about 5 min). An unstable brain state may be attested by a somatic indication of an epileptic seizure, aura, or other unstable brain state, but need not be. An unstable brain state may be attested by an electroencephalographic (EEG) indication of an epileptic seizure, aura, or other unstable brain state, but need not be. An unstable brain state encompasses both a state after which an epileptic seizure is highly likely or even inevitable, as well as a state in which an otherwise highly likely or inevitable epileptic seizure can be prevented by the application of a therapeutic electrical signal to nervous tissue, such as the brain or a cranial or peripheral nerve. However, an unstable brain state may be declared with a reasonable degree of accuracy from somatic indications, and in a particular embodiment, from at least one cardiac parameter, in light of at least a first value.

The cardiac module 296 is capable of determining at least a first cardiac parameter based upon sensed cardiac data from the patient, as discussed above.

The value setting module 282 sets at least a first value to be used by the unstable brain state declaration module 280. The at least a first value, along with the at least a first cardiac parameter determined by the cardiac module 296, is used by the unstable brain state declaration module 280 to declare or not declare the occurrence of an unstable brain state. For example, the at least a first cardiac parameter may be a moving average of the patient's heart rate (by way of example only, having a baseline value of 60-75 BPM) and the at least a first value may be a heart rate threshold value (by way of example only, 120 BPM). At a predetermined sampling rate, by way of example, from about 100 times per second to about once per five seconds, the cardiac module 296 determines the moving average of the patient's heart rate and the unstable brain state declaration module 280 compares the moving average of the patient's heart rate to the heart rate threshold value. If, by way of example only, the moving average of the patient's heart rate is 125 BPM, which is greater than the heart rate threshold value of this example, the unstable brain state declaration module 280 declares that an unstable brain state has occurred. If, by way of example only, the moving average of the patient's heart rate is 80 BPM, which is less than the heart rate threshold value of this example, the unstable brain state declaration module 280 does not declare an unstable brain state to have occurred.

In one embodiment, the memory 217 is capable of storing a timestamp associated with a declaration of an unstable brain state by the unstable brain state declaration module 280. The memory 217 may also be capable of storing a time series of the at least one cardiac parameter and/or the at least a first value. The unstable brain state declaration module 280, or another module in the IMD 200 or in an apparatus in communication with the IMD 200 (such as the computer 150), may create a log of times at which a patient experiences an unstable brain state.

In addition to the heart rate threshold value discussed above, the at least a first value may also comprise a minimum duration of an elevation of heart rate, a threshold rate of change of heart rate, or any combination of cardiac and/or non-cardiac values. The at least a first value may be a logical or Boolean value, a set of logical or Boolean values, or a combination of one or more logical or Boolean values and one or more alphanumeric values. In embodiments in which the IMD 200 collects multiple parameters, such as multiple cardiac parameters, or both at least one cardiac parameter and at least one non-cardiac parameter (discussed below), the at least a first value may also comprise either or both of weightings for each of the multiple parameters, and logical relationships between each of the multiple parameters.

The value setting module 282 is capable of adjusting the at least first value. The determination of the different value may be made by a medical professional, by the patient, or by the IMD 200 itself. For example, continuing the above example, if the patient experienced a seizure correlated with an increase in the patient's heart rate to 115 BPM (below the heart rate threshold value of 120 BPM, and hence, with no declaration of an unstable brain state), the value setting module 282 may adjust the heart rate threshold value to 115 BPM, 110 BPM, or some other value. Such adjustment would render the unstable brain state determination module more likely to declare an unstable brain state.

Alternatively in the above example, if the patient experienced a heart rate above the heart rate threshold value of 120 BPM, and hence, an unstable brain state was declared, but the patient's elevated heart rate was caused by volitional physical exertion, an intense emotional response, or another cause not associated with an unstable brain state, the value setting module 282 may adjust the heart rate threshold value to 125 BPM, 130 BPM, or some other value. Such adjustment would render the unstable brain state determination module less likely to declare an unstable brain state.

Continuing with the above example, the decision to adjust the heart rate threshold may be made by a medical professional or by the patient, such as at a time shortly after the seizure or at a later time when a log of the patient's at least one cardiac parameter is analyzed. In other words, in this embodiment, the value setting module 282 is capable of adjusting the at least a first value in response to a user request to adjust the at least a first value.

The present invention gives a user, such as a patient or a medical professional, great flexibility in deciding how to respond to uncertainty inherent in the assessment of whether or not an unstable brain state has occurred. A user may set the at least a first value such that the unstable brain state declaration module 280 declares unstable brain states with any desired level of aggressiveness or certainty. For example, a user may accept a high "false positive" rate and want the unstable brain state declaration module 280 to declare every putative unstable brain state; contrarily, a user may desire a low "false positive" rate and want the unstable brain state declaration module 280 to only declare an unstable brain state with very high certainty, or even to declare only particular kinds of unstable brain states, such as relatively severe epileptic seizures as opposed to all seizures. Thus, the present invention provides the user a great deal of flexible control over the stringency of declarations of unstable brain states.

Having the benefit of the present disclosure, the person of ordinary skill in the art would be able to set and adjust the at least a first value as a matter of routine experimentation.

In one embodiment, the adjustment may be made by a unit of the value setting module 282 on a determination of an unstable brain state from other data, such as other cardiac data (e.g., an elevation of heart rate above the patient's baseline heart rate for a predetermined or adjustable duration, or a difference between a first moving average and a second moving average, among others) or other data (e.g., an output from an accelerometer measuring acceleration of the patient's limbs, torso, or head, wherein the output is indicative of a seizure; or an output from electromyography of one or more muscles, wherein the output is indicative of a seizure; among others).

As discussed above, the value setting module 282 is capable of adjusting the at least a first value to render the unstable brain state declaration module 280 less likely to declare an unstable brain state. Rendering the unstable brain state declaration module 280 less likely to declare an unstable brain state may lead to fewer overall declarations of unstable brain states or a delay in a declaration of an unstable brain state, among other possible outcomes. This may be desirable, for example, when a healthcare provider desires to use the IMD as a seizure diary and wishes to avoid declaring an unstable brain state unless and until an epileptic seizure actually occurs, or when the device responds to the declaration of an unstable brain state by providing vagus nerve stimulation, but the patient has difficulty tolerating the therapy thus provided. Adjusting the first value to reduce the likelihood of a declaration of an unstable brain state may lead to fewer false declarations of unstable brain states. Such an adjustment may, however, risk actual occurrences of unstable brain states that are not declared, i.e., may lead to more "false negatives," with an associated increased risk that an epileptic seizure would occur without therapy being administered or being administered late.

As stated above, rendering the unstable brain state declaration module 280 less likely to declare an unstable brain state may in some embodiments lead to a delay in a declaration of an unstable brain state. A delay in declaration may be advantageous by giving greater certainty to the patient or physician that a declaration is made when an unstable brain state is actually occurring. However, this does represent a trade-off against earlier declaration of an unstable brain state. For example, if the declaration of an unstable brain state is followed by a therapeutic electrical signal intended to intervene in the unstable brain state, a delay in declaration may lead to a shorter time window for delivering the therapeutic electrical signal or a requirement for the therapeutic electrical signal to have a higher amplitude, frequency, on-time, or other parameter than would be required if the therapy were provided sooner.

Similarly, as discussed above, the value setting module 282 is capable of adjusting the at least a first value to render the unstable brain state declaration module 280 more likely to declare an unstable brain state. Rendering the unstable brain state declaration module 280 more likely to declare an unstable brain state may lead to more overall declarations of unstable brain states or faster declaration of an unstable brain state, among other possible outcomes. Such an adjustment may be desirable where a patient experiences severe epileptic seizures, and it is important to intervene with a therapy such as vagus nerve stimulation as early as possible with the goal of avoiding or reducing the severity of the seizure, even if some occasions of "false positives" occur in which a seizure would not have occurred even absent the therapy intervention. Adjusting the first value to increase the likelihood of a declaration of the occurrence of an unstable brain state may lead to fewer unstable brain states actually leading to seizures, though one or more false declarations of unstable brain states may result, along with an increase in unnecessary therapy interventions.

As should be apparent to the person of ordinary skill in the art, rendering the unstable brain state declaration module 280 more likely to declare an unstable brain state may lead to a faster declaration of an unstable brain state. A faster declaration may be advantageous by giving a longer time window for delivering a therapeutic electrical signal or by allowing the therapeutic electrical signal to have a lower amplitude, frequency, on-time, or other parameter than if the therapy were provided later. However, this does represent a trade-off against later declaration of an unstable brain state. For example, faster declaration of an unstable brain state may reduce the certainty to the patient or physician that a declaration is made when an unstable brain state is actually occurring.

Alternatively or in addition to use of at least one cardiac parameter and at least a first value to declare an unstable brain state, in one embodiment, the unstable brain state declaration module 280 may determine at least one non-cardiac parameter and at least a second value. The at least one non-cardiac parameter and at least a second value may either be used in a calculation to confirm or deny a declaration of an unstable brain state based on the at least one cardiac parameter and the at least a first value, or may be used in combination with the at least one cardiac parameter and the at least a first value in making the declaration of an unstable brain state. Alternatively or in addition, the at least one non-cardiac parameter and at least a second value may be used to make a "shadow" or putative declaration of an unstable brain state, against which declarations of unstable brain states using the at least one cardiac parameter can be compared by a medical professional or the IMD to assist in adjusting the at least a first value. Returning to the above example, wherein the at least a first value is a heart rate threshold value, the "shadow" declaration of an unstable brain state can be the basis for a decision to raise or lower the heart rate threshold value.

In one embodiment, the unstable brain state declaration module 280 may further comprise a non-cardiac parameter detection module (not shown) capable of detecting an activity level of the patient.

In one embodiment, the unstable brain state declaration module 280 may further comprise a non-cardiac parameter detection module capable of detecting an output of an accelerometer. The accelerometer may be worn on the patient's person or implanted in the patient's body.

In one embodiment, the unstable brain state declaration module 280 may further comprise a non-cardiac parameter detection module capable of detecting a catamenial cycle. The parameter detection module of this embodiment may detect the presence of hormones associated with the catamenial cycle, the patient's basal temperature, the patient's or her physician's observation of events indicative of various points in her catamenial cycle, or other data indicative of the patient's catamenial cycle.

In one embodiment, the unstable brain state declaration module 280 may further comprise a non-cardiac parameter detection module capable of detecting the time of day. The parameter detection module of this embodiment may be a clock or a module capable of querying a clock for the current time.

In one embodiment, the unstable brain state declaration module 280 may further comprise a non-cardiac parameter detection module capable of detecting an indicator of the patient's sleep state. Exemplary indicators of the patient's sleep include electroencephalogram (EEG) signals associated with sleep and rapid eye movements associated with REM sleep, among others.

In one embodiment, the unstable brain state declaration module 280 may further comprise a non-cardiac parameter detection module capable of detecting an inclination of the patient's body.

In one embodiment, the unstable brain state declaration module 280 may further comprise a non-cardiac parameter detection module capable of detecting a dilation of a pupil of the patient.

In one embodiment, the unstable brain state declaration module 280 may further comprise a non-cardiac parameter detection module capable of detecting the patient's body temperature.

In one embodiment, the unstable brain state declaration module 280 may further comprise a non-cardiac parameter detection module capable of detecting the patient's blood pressure.

In one embodiment, the unstable brain state declaration module 280 may further comprise a non-cardiac parameter detection module capable of detecting the patient's electroencephalogram (EEG).

In one embodiment, the unstable brain state declaration module 280 may further comprise a non-cardiac parameter detection module capable of detecting at least one non-cardiac parameter selected from the group consisting of an activity level of the patient, an output of an accelerometer, a catamenial cycle, the time of day, an indicator of the patient's sleep state, an inclination of the patient's body, a dilation of a pupil of the patient, the patient's body temperature, the patient's blood pressure, and the patient's electroencephalogram (EEG).

As stated above, in embodiments wherein the unstable brain state declaration module 280 uses multiple parameters, the at least a first value may relate to weightings of or logical relationships between the multiple parameters. For example, if an accelerometer (A) has been inactive and heart rate (R) begins to increase rapidly, the at least a first value may be a logical value boolHeartRateIncreaseWithoutActivity set to true, and the unstable brain state declaration module 280 may declare an unstable brain state from the logical value being true. However if an accelerometer indicates high activity level and then heart rate begins to increase rapidly, a logical value boolHeartRateIncreaseWithoutActivity may be set to false, and the unstable brain state declaration module 280 may not declare an unstable brain state from the logical value being false. More aggressive users may desire a logical value boolHeartRateIncrease=true or one of a pair of logical values (boolHeartRateIncrease=true or boolActivity=true) to be sufficient for the unstable brain state declaration module 280 to declare an unstable brain state.

In embodiments wherein the unstable brain state declaration module 280 further comprises a non-cardiac parameter detection module, the value setting module 282 may be capable of setting at least a second value, and the unstable brain state declaration module 280 is capable of declaring an unstable brain state of the patient from both said at least one non-cardiac parameter and said at least a second value. For example, the second value may be an acceleration threshold of a limb; if an accelerometer implanted in the limb reports an acceleration greater than the acceleration threshold, the unstable brain state declaration module 280 in this example may declare an unstable brain state on the assumption the limb acceleration results from uncontrolled contraction of one or more skeletal muscles in the limb.

In one embodiment, the at least one non-cardiac parameter and the at least a second value can be used by the value setting module 282 to adjust the at least a first value, the at least a second value, or both. Alternatively or in addition, in embodiments wherein the memory 217 is capable of storing a timestamp at which a patient experienced an unstable brain state declared by the unstable brain state declaration module 280, the timestamp or a log of timestamps can be used by the value setting module 282 to adjust the at least a first value, the at least a second value, or both. In other words, in one embodiment the value setting module 282 is capable of adjusting the at least a first value, the at least a second value, or both based upon at least one factor selected from the group consisting of a timestamp at which a patient experienced an unstable brain state, cardiac data associated with a timestamp at which a patient experienced an unstable brain state, an activity level of the patient, an output of an accelerometer, a catamenial cycle, the time of day, an indicator of the patient's sleep, an inclination of the patient's body, a dilation of a pupil of the patient, the patient's body temperature, the patient's blood pressure, and the patient's electroencephalogram (EEG).

A patient may experience changes in the frequency of unstable brain states over various periods of time. For example, a patient may have an increased frequency of unstable brain states during certain hours of the day, certain days of the week or month, certain seasons of the year, or over longer periods of time as the patient's disease state changes. In one embodiment, the value setting module 282 is capable of analyzing a log of times at which a patient experiences an unstable brain state to determine at least a first period when the patient has an increased frequency of unstable brain states, and adjusting the at least a first value to render the unstable brain state declaration module 280 more likely to declare an unstable brain state during said at least a first period. The first period may be less than one day. In other embodiments, the first period may be less than one week, less than one month, or less than one year.

The value setting module 282 may comprise other modules than those described above.

The IMD 200 described above, and methods described herein, are useful in providing a user, such as a patient or a medical professional, with information regarding the patient's unstable brain states. Such information may assist the patient and the medical professional in improving the patient's treatment regimen or improving the patient's quality of life. The information regarding the patient's unstable brain states may include an alert to the patient and/or his caregiver that an epileptic seizure is likely, giving the patient and/or his caregiver some time to prepare for the epileptic seizure and its aftermath.

In one embodiment, the electrical signal generator of the implantable medical device is capable of generating and delivering at least a first electrical signal through at least the first electrode to the vagus nerve if an unstable brain state has not been declared, and generating and delivering at least a second electrical signal through at least the first electrode to the vagus nerve if an unstable brain state has been declared. The first electrical signal can be a conventional VNS signal for the chronic treatment of epilepsy. The second electrical signal can be an active VNS signal for the prevention or reduction in severity of an epileptic seizure. The second electrical signal can have a greater pulse amplitude, a wider pulse width, a higher pulse frequency, a greater number of pulses per burst, a higher on time/off time ratio, or two or more thereof, relative to a conventional VNS signal. Such a second electrical signal would consume more electrical power than a conventional VNS signal and could be attenuated by adaptation thereto by neurons of the vagus nerve if the second electrical signal were continuously applied. However, if the second electrical signal were applied only when an unstable brain state is declared, the duration of application would be expected to be short enough that adaptation thereto would be unlikely, and the increased consumption of electrical power would be likely to be offset by a reduction in the number, severity, or both of the patient's seizures and an accompanying improvement in the patient's quality of life. The adjustability of the at least a first value would allow considerations of IMD battery life to be included in the actions of the value setting module 282.

Figure 4:
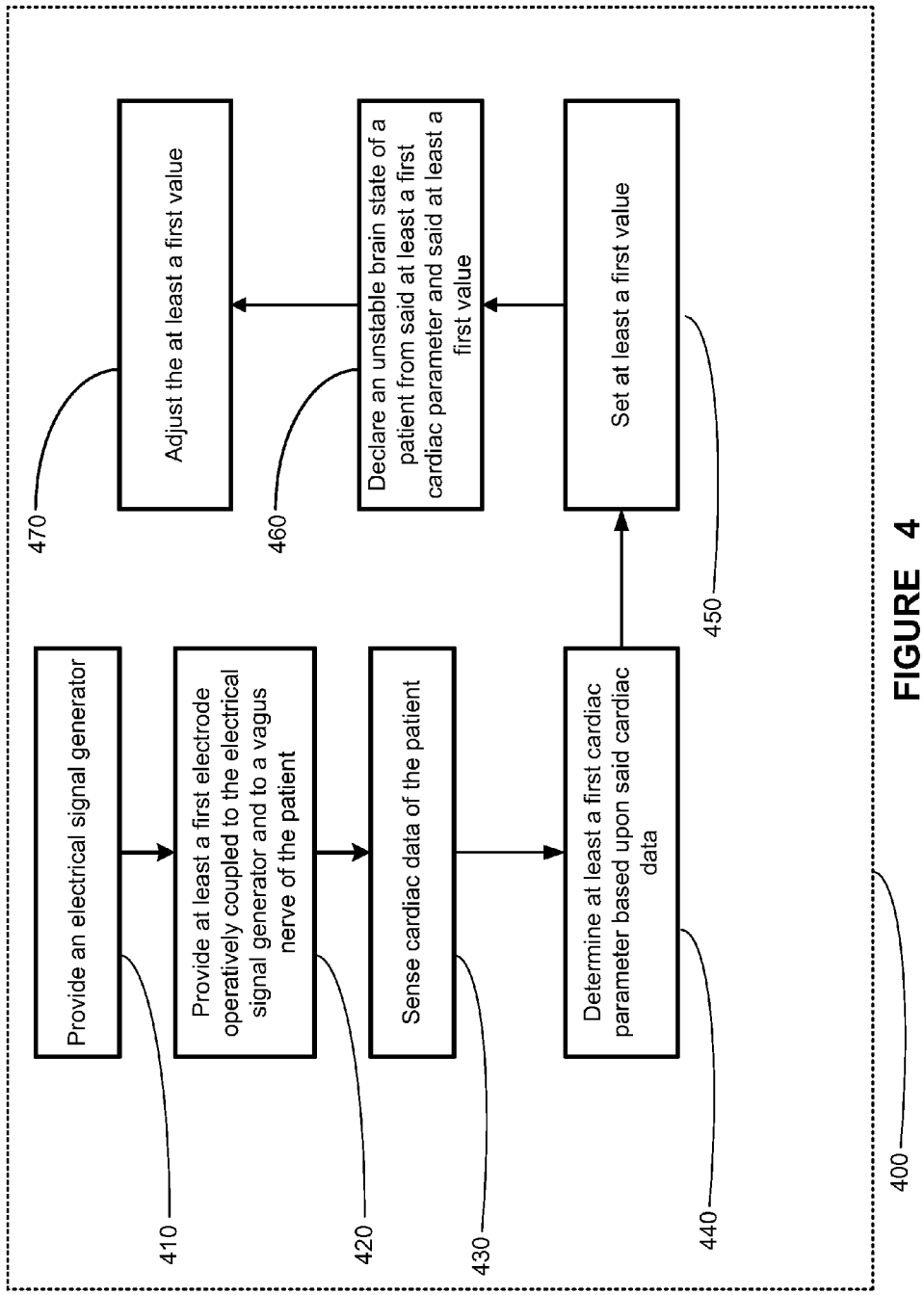
FIG. 4 illustrates a flowchart depiction of a method in accordance with an illustrative embodiment of the present invention.

In one embodiment, as shown in FIG. 4, the present invention relates to a method 400 of treating a medical condition in a patient using an implantable medical device 200, comprising providing 410 an electrical signal generator; providing 420 at least a first electrode operatively coupled to the electrical signal generator and to a vagus nerve of the patient; sensing 430 cardiac data of the patient; determining 440 at least a first cardiac parameter based upon said cardiac data; setting 450 at least a first value; declaring 460 an unstable brain state of a patient from said at least a first cardiac parameter and said at least a first value; and adjusting 470 the at least a first value.

Figure 5:
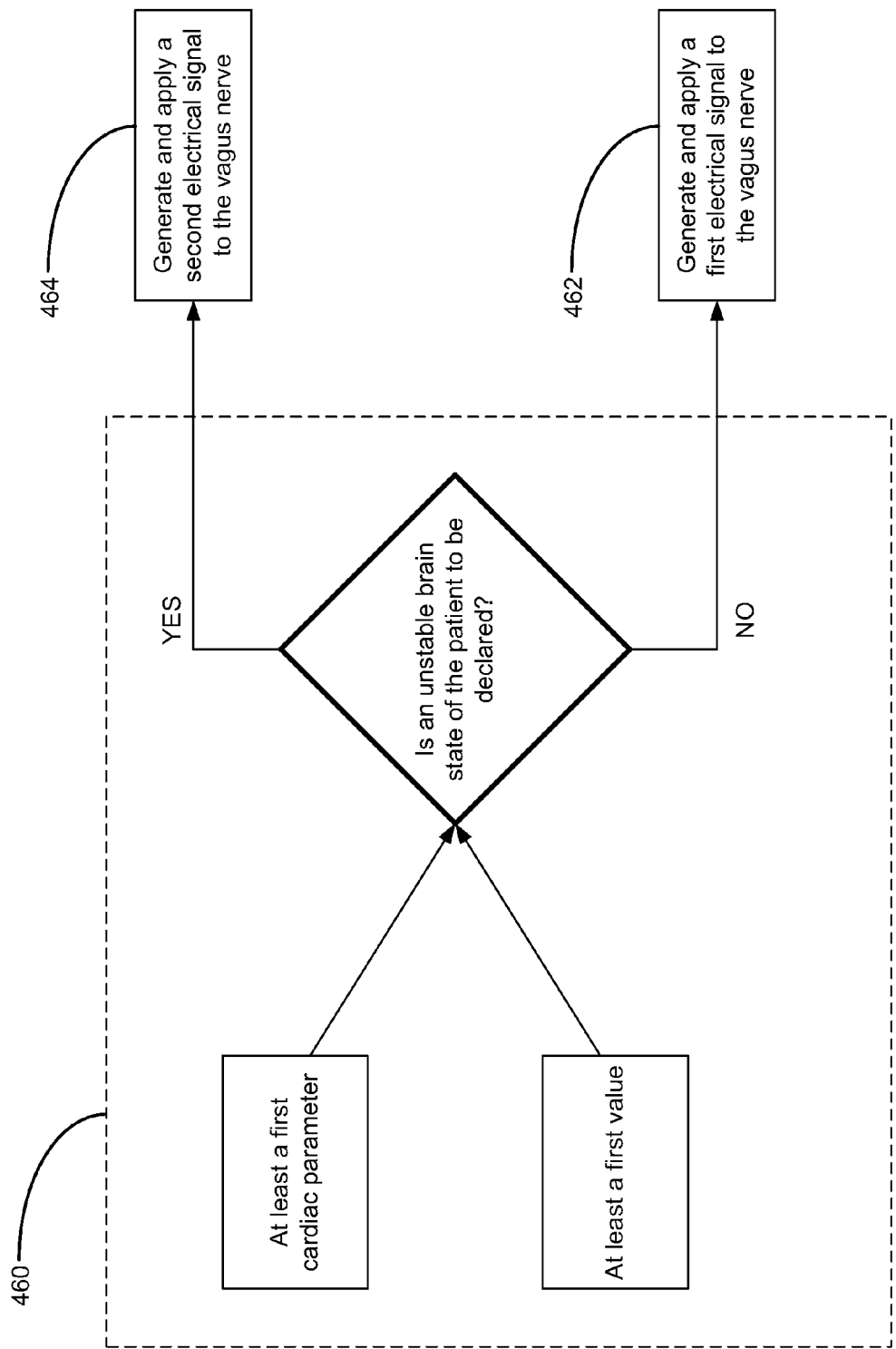
FIG. 5 illustrates a flowchart depiction of further steps of a method in accordance with an illustrative embodiment of the present invention.

In one embodiment, the method can further comprise generating and applying 462 a first electrical signal to the vagus nerve if an unstable brain state has not been declared, and generating and applying 464 a second electrical signal to the vagus nerve if an unstable brain state has been declared. FIG. 5 shows this embodiment.

In one embodiment, sensing 430 cardiac data comprises sensing at least one of a P wave, an Q wave, a QR complex, an R wave, an S wave, a QRS complex, a T wave, and a U wave, and wherein said at least a first cardiac parameter comprises at least one of an instantaneous heart rate, a moving average heart rate over a predetermined time period, a ratio of a first moving average heart rate over a first predetermined time period and a second moving average heart rate over a second predetermined time period, a rate of change of the patient's heart rate, an elevation of the patient's instantaneous heart rate above a baseline heart rate, a duration of an elevation of the patient's heart rate above the patient's baseline heart rate, a duration of an elevation of a first moving average heart rate over a second moving average heart rate, an R-R interval, a P-P interval, a PR segment interval, a PQ segment interval, a QRS interval, an ST segment interval, a QT interval, a statistical analysis heart parameter, a spectral analysis heart parameter, a fractal analysis heart parameter, and two or more thereof.

In one embodiment, adjusting 470 the at least a first value occurs in response to a user request to adjust the first value.

In one embodiment, adjusting 470 the at least a first value comprises rendering declaring an unstable brain state less likely and/or less quickly. In another embodiment, adjusting 470 the at least a first value comprises rendering declaring an unstable brain state more likely and/or more quickly.

In one embodiment, the method further comprises storing a timestamp associated with declaring an unstable brain state. In one further embodiment, adjusting the at least a first value is based upon a plurality of the timestamps. In another further embodiment, the method further comprises storing a time series of the at least a first cardiac parameter.

In one embodiment, the method further comprises determining at least a first period when the patient has an increased frequency of unstable brain states, and adjusting the at least a first value to render declaring an unstable brain state more likely during said at least a first period.

In one embodiment, the present invention relates to a computer readable program storage device encoded with instructions that, when executed by a computer, performs a method of treating a medical condition in a patient using an implantable medical device, comprising; sensing cardiac data of the patient; determining at least a first cardiac parameter based upon said cardiac data; setting at least a first value; declaring an unstable brain state of a patient from said at least a first cardiac parameter and said at least a first value; and adjusting the at least a first value.

The method executed by the computer may provide a log of unstable brain states or an alert of an unstable brain state.

In one embodiment of the computer readable program storage device, the method further comprises, if an unstable brain state is not declared, instructing an electrical signal generator to generate and deliver a first electrical signal through at least the first electrode to the vagus nerve of the patient, and if an unstable brain state is declared, instructing an electrical signal generator to generate and deliver a second electrical signal through at least the first electrode to the vagus nerve of the patient.

Using embodiments of the present invention, a therapeutic regimen comprising neurostimulation may be enhanced and optimized. Using certain embodiments, data either directly or indirectly associated with an acute incident of a medical condition may be collected, in order to inform the patient and/or his physician about the severity, progression, or remission of the medical condition.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be apparent that the principles of the invention may be applied to selected cranial nerves other than, or in addition to, the vagus nerve to achieve particular results in treating patients having epilepsy, depression, or other medical conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed is:

1. An medical device comprising:
    a cardiac data sensing module operable to sense cardiac data;
    a value setting module operable to set a first cardiac threshold value and dynamically adjust the first cardiac threshold value based upon sensed cardiac data from the cardiac sensing module;
    a cardiac module operable to determine a first cardiac parameter based upon sensed cardiac data from the cardiac sensing module;
    an unstable brain state declaration module operable to declare a seizure when the first cardiac parameter exceeds the first cardiac threshold value.

2. The medical device of claim 1, wherein:
    the value setting module is operable to set a second cardiac threshold value and dynamically adjust the second cardiac threshold value based upon sensed cardiac data from the cardiac data sensing module;
    the cardiac module is operable to determine a second cardiac parameter based upon sensed cardiac data; and
    the unstable brain state declaration module is further operable to declare a seizure when the second cardiac parameter exceeds the second cardiac threshold value.

3. The medical device of claim 1, further comprising:
    a non-cardiac data sensing module operable to sense non-cardiac data;
    the value setting module operable to set a first non-cardiac threshold value and dynamically adjust the first non-cardiac threshold value based upon sensed non-cardiac data from the non-cardiac sensing module;
    a non-cardiac module operable to determine a first non-cardiac parameter based upon sensed non-cardiac data from the non-cardiac data sensing module; and
    the unstable brain state declaration module operable to declare an a seizure when the first non-cardiac parameter exceeds the first non-cardiac threshold value.

4. The medical device of claim 3, wherein:
    the value setting module is further operable to apply a weighting factor to the first cardiac threshold value and the first non-cardiac threshold value; and
    the unstable brain state declaration module is operable to utilize the weighted first cardiac threshold value and the first non-cardiac threshold value in declaring a seizure.

5. The medical device of claim 3, wherein the first non-cardiac parameter is selected from the group comprising:
    an activity level;
    an output of an accelerometer;
    a catamenial cycle;
    a time of day;
    an indicator of a sleep state;
    an inclination of a body;
    a pupil dilation;
    a body temperature;
    a blood pressure; and
    an electroencephalogram (EEG).

6. The medical device of claim 1, wherein the value setting module sets the first cardiac threshold value in response to a user request to set the first cardiac threshold value.

7. The medical device of claim 1, wherein the value setting module adjusts the first cardiac threshold value in response to a user request to adjust the first cardiac threshold value.

8. The medical device of claim 1, wherein the value setting module is operable to adjust the first cardiac threshold value to render the unstable brain state declaration module more likely to declare a seizure.

9. The medical device of claim 1, wherein the value setting module is operable to adjust the first cardiac threshold value to render the unstable brain state declaration module less likely to declare a seizure.

10. The medical device of claim 1, wherein the first cardiac parameter is selected from the group comprising:
an instantaneous heart rate;
a moving average heart rate over a predetermined time period;
a ratio of a first moving average heart rate over a first predetermined time period and a second moving average heart rate over a second predetermined time period;
a rate of change of a heart rate;
an elevation of an instantaneous heart rate above a baseline heart rate;
a duration of an elevation of a heart rate above a baseline heart rate;
a depression of a heart rate below a baseline heart;
a duration of an elevation of a first moving average heart rate over a second moving average heart rate;
an R-R interval;
a PR segment interval;
a PQ segment interval;
a QRS interval;
an ST segment interval;
a statistical analysis heart parameter;
a spectral analysis heart parameter;
a fractal analysis heart parameter;
an interbeat interval;
an amplitude or a magnitude of a P wave, Q wave, R wave, S wave, T wave, U wave;
a change in amplitude or a magnitude of a P wave, Q wave, R wave, S wave, T wave, U wave; and
a rate of change an amplitude or magnitude of a P wave, Q wave, R wave, S wave, T wave, U wave.

11. The medical device of claim 1, further comprising a memory that stores a timestamp associated with a declaration of a seizure.

12. The medical device of claim 11, wherein the value setting module is further configured to adjust a threshold value based upon the timestamp at which a seizure is declared.

13. The medical device of claim 11, wherein the value setting module is further configured to:
perform an analysis of a log of times at which a seizure was declared to determine a first period when an increased frequency of seizure declarations are likely to occur; and
adjust the first cardiac threshold value to render the unstable brain state declaration module more likely to declare a seizure during the first period.

14. The medical device of claim 1, wherein the medical device comprises an implantable medical device (IMD).

15. A method of declaring a seizure using a medical device, comprising:
sensing cardiac data;
setting a first cardiac threshold value based upon the sensed cardiac data;
dynamically adjusting the first cardiac threshold value based upon the sensed cardiac data;
determining a first cardiac parameter based upon the sensed cardiac data; and
declaring a seizure in response to the first cardiac parameter exceeding the first cardiac threshold value.

16. The method of claim 15, further comprising:
setting a second cardiac threshold value based upon the sensed cardiac data;
dynamically adjusting the second cardiac threshold value based upon the sensed cardiac data;
determining a second cardiac parameter based upon the sensed cardiac data; and
declaring a seizure in response to the second cardiac parameter satisfying the second cardiac threshold value.

17. The method of claim 16, further comprising:
applying a weighting factor to the first cardiac threshold value and the second cardiac threshold value; and
utilizing the weighted first cardiac threshold value and the weighted second cardiac threshold value in declaring seizure.

18. The method of claim 15, further comprising storing a timestamp associated with declaring a seizure.

19. The method of claim 18, further comprising adjusting a threshold value based upon the timestamp at which a seizure is declared.

20. The method of claim 18, further comprising:
performing an analysis of a log of times at which a seizure was declared to determine a first period when an increased frequency of seizure declarations are likely to occur; and
adjusting the first cardiac threshold value to render the unstable brain state declaration module more likely to declare a seizure during the first period.

* * * * *